(12) United States Patent
Kothakonda et al.

(10) Patent No.: US 7,863,442 B2
(45) Date of Patent: Jan. 4, 2011

(54) PROCESSES FOR THE SYNTHESIS OF OLANZAPINE

(75) Inventors: Kiran Kumar Kothakonda, Brantford (CA); Daqing Che, Brantford (CA); Bhaskar Reddy Guntoori, Brantford (CA)

(73) Assignee: Apotex Pharmachem Inc., Brantford (CA)

( * ) Notice: Subject to any disclaimer, the term of this patent is extended or adjusted under 35 U.S.C. 154(b) by 663 days.

(21) Appl. No.: 11/976,978

(22) Filed: Oct. 30, 2007

(65) Prior Publication Data

US 2008/0319189 A1 Dec. 25, 2008

(30) Foreign Application Priority Data

Jun. 22, 2007 (CA) .................................. 2593407

(51) Int. Cl.
*C07D 495/02* (2006.01)

(52) U.S. Cl. ...................................................... 540/557
(58) Field of Classification Search .................. 540/557
See application file for complete search history.

(56) References Cited

U.S. PATENT DOCUMENTS

| 5,229,382 A | 7/1993 | Chakrabarti et al. |
| 2004/0048854 A1 | 3/2004 | Patel et al. |
| 2005/0159408 A1 | 7/2005 | Dolitzky et al. |

FOREIGN PATENT DOCUMENTS

EP 454436 B1 9/1995

*Primary Examiner*—Brenda L Coleman

(57) ABSTRACT

There is provided a process for the preparation of olanzapine comprising:
  i) reacting 4-amino-2-methyl-10H-thieno-[2,3-b][1,5] benzodiazepine and N-methylpiperazine in a $C_1$ to $C_4$ alcoholic solvent or mixture thereof at suitable temperature and for a suitable time,
  ii) cooling the reaction mixture, and
  iii) isolating the precipitated olanzapine.

10 Claims, No Drawings

PROCESSES FOR THE SYNTHESIS OF OLANZAPINE

BACKGROUND OF THE INVENTION

Olanzapine (1,2-methyl-4-(4-methyl-1-piperazinyl)-10H-thieno[2,3-b][1,5]benzodiazepine) is a second generation anti-psychotic drug marketed as Zyprexa® by Eli Lilly and Company. It is useful for the treatment of disorders such as schizophrenia, bipolar disorder, psychotic depression and Tourette syndrome. This pharmaceutical acts as an antagonist on $5-HT_2$ serotonin receptors as well as the $D_1/D_2$ dopamine receptors and also exhibits anticholinergic and antimuscarine properties.

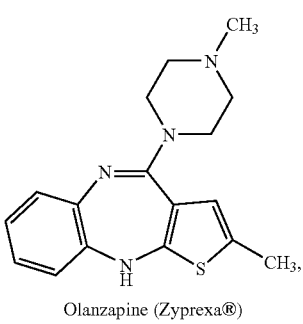

Olanzapine (Zyprexa®)

Structurally olanzapine belongs to the benzodiazepine family. The synthesis of olanzapine was disclosed, for example, in U.S. Pat. No. 5,229,382, involving the condensation of 4-amino-2-methyl-10H-thieno-[2,3-b][1,5]benzodiazepine and N-methylpiperazine in a mixture of the high boiling and aprotic solvents, dimethylsulfoxide and toluene (Scheme 1). However, this process suffers from the use of high volumes of solvents and the necessity of having a large excess of N-methylpiperazine. Of equal importance is the low yield (less than 35%) and poor recoverability of the dimethylsulfoxide solvent.

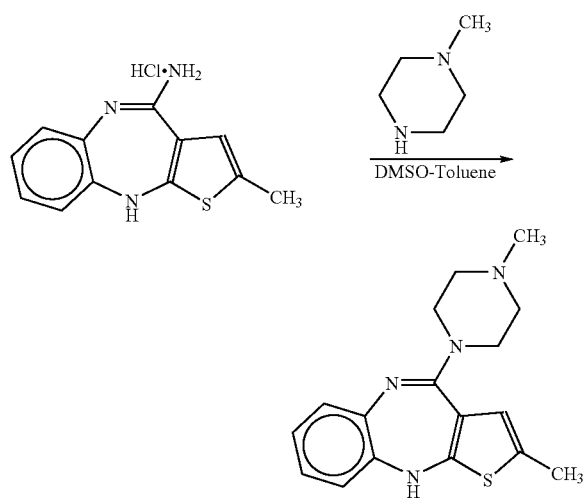

EP 454436 B1 discloses the synthesis of olanzapine via the titanium tetrachloride ($TiCl_4$)-mediated reaction of N-methylpiperazine and methyl-2-(2-aminoanilino)-5-methylthiophene-3-carboxylate. The use of the toxic and environmentally hazardous reagent $TiCl_4$ makes the process unattractive on an industrial scale.

US 2004/0048854 A1 teaches a modified process for the preparation of olanzapine using only dimethylsulfoxide as the solvent, but this process requires tedious work-up steps employing acid and base treatments, and halogenated solvents. Also, like the route described in U.S. Pat. No. 5,229,382, the dimethylsulfoxide solvent is very difficult to recover.

US 2005/0159408 discloses a method of synthesizing olanzapine without using solvent, where N-methylpiperazine is used in large excess and the reaction occurred under harsh conditions (high temperature over 125° C.). Again the work-up is tedious and some solvents, like dimethylsulfoxide used in the work-up, have poor recoverability. In the same patent application, processes for preparing olanzapine are disclosed where low boiling organic solvents such as acetone, acetonitrile, hexane, heptane and dimethylformamide are used and the yield, ranged from 51% to 91%. However, the product is isolated in granular form and the purity is not reported.

Therefore, it is an object of the present invention to develop a robust and high-yielding process for producing olanzapine which is suitable for commercial scale production and overcomes the deficiencies in the prior art processes.

Further and other objects of the invention will become apparent to those skilled in the art when considering the following summary of the invention and the more detailed description of the embodiments of the invention described herein.

SUMMARY OF THE INVENTION

According to one aspect of the invention, there is provided a process for the preparation of olanzapine comprising:
i) reacting 4-amino-2-methyl-10H-thieno-[2,3-b][1,5] benzodiazepine and N-methylpiperazine in a $C_1$ to $C_4$ alcoholic solvent or mixture thereof at suitable temperature and for a suitable time,
ii) cooling the reaction mixture, and
iii) isolating the precipitated olanzapine.

Optionally, water is added to the reaction mixture and the precipitated olanzapine is isolated.

Surprisingly, we have found that low boiling alcohols represent highly desirable solvents for the condensation reaction of 4-amino-2-methyl-10H-thieno-[2,3-b][1,5]benzodiazepine and N-methylpiperazine. The advantages of these solvents relative to the processes of the prior art include: 1) environmentally friendly solvents are employed; 2) toxic reagents, like $TiCl_4$, are not required; 3) solvents can be easily recovered and re-used; and 4) the olanzapine produced is isolated in high yield and purity.

According to another aspect of the invention, the use of a $C_1$ to $C_4$ alcohol as the reaction medium in the process results in a surprisingly rapid reaction completion, permitting the use of relatively low temperatures and allowing reduced process cycle times. Moreover, the use of a $C_1$ to $C_4$ alcohol as a reaction medium for the processes of the instant invention furnishes olanzapine which meets the high purity (>99.5%) specifications for use as a pharmaceutical active.

According to yet another aspect of the invention, since $C_1$ to $C_4$ alcohols are largely water miscible, the work-up procedure is streamlined because water can be employed as an effective anti-solvent to precipitate the olanzapine product.

In a preferred embodiment, olanzapine can be produced by reacting 4-amino-2-methyl-10H-thieno-[2,3-b][1,5]benzodiazepine with N-methylpiperazine in a $C_1$ to $C_4$ alcoholic solvent or solvent mixture at suitable temperature and for a suitable time. The $C_1$ to $C_4$ alcoholic solvent can be selected from methanol, ethanol, n-propanol, 2-propanol and 2-butanol, n-butanol, isobutanol, and tert-butanol, and combinations thereof. The most preferred alcoholic solvents are 2-propanol and 2-butanol. The volume of the solvent used can be 1 to 8 volumes, preferably 2 to 6 volumes, and most preferably 2 to 4 volumes. The volume of N-methylpiperazine used can be 1 to 5 volumes, more preferably 2 to 3 volumes, and most preferably 2 to 2.5 volumes. The term volumes refers to litres of solvent per kilograms of 4-amino-2-methyl-10H-thieno-[2,3-b][1,5]benzodiazepine.

The reaction temperature can be between about 50° C. to about 150° C., preferably about 80° C. to about 120° C., and most preferably about 90° C. to about 120° C.

The reaction time can range from 5 to 30 hours, preferably 10 to 25 hours and most preferably 10 to 20 hours.

In another embodiment of the invention, after reaction completion, the reaction mixture can be cooled to 0° C. to 75° C., more preferably 10° C. to 65° C., and most preferably 20° C. to 60° C., wherein the product can be isolated by direct filtration; or optionally water can be added as an anti-solvent to facilitate precipitation and isolation by filtration. For the processes where water is used to effect precipitation, the amount of water required can be 0.1 to 8 volumes, preferably 0.5 to 6 volumes, and most preferably 1 to 4 volumes, wherein volumes has the same meaning as set out above. The use of water as an anti-solvent has the additional unexpected advantage of removing the synthetic by-products and the reaction solvent. Filtration of the product and washing with water also avoids a tedious liquid-liquid extractive work-up which represents a deficiency in prior art processes.

The following non-limiting examples further illustrate the manner of carrying out the inventive processes described herein.

EXAMPLE 1

4-Amino-2-methyl-10H-thieno-[2,3-b][1,5]benzodiazepine (50 g, 0.19 mol), N-methylpiperazine (125 mL, 2.5 vol) and 2-propanol (150 mL, 3 vol) were charged into a three-necked round bottom flask, equipped with reflux condenser, overhead stirrer, and thermometer. The reaction mixture was heated to reflux (about 100° C.) slowly under a nitrogen atmosphere and then refluxed overnight. The reaction mixture was allowed to cool slowly to below 40° C. (about 1 h), whereupon solid precipitates out. This precipitate was then isolated by filtration and the resulting light yellow solid was twice washed with 2-propanol (100 mL). The light yellow solid was stirred with water (4 volumes) for 2.5 hours, filtered, and the resulting solid, was washed twice with water (2 volumes) and dried to furnish olanzapine (47 g, 80%).

EXAMPLE 2

4-Amino-2-methyl-10H-thieno-[2,3-b][1,5]benzodiazepine (100 g, 0.38 mol), N-methylpiperazine (250 mL, 2.5 vol) and 2-butanol (200 mL, 2 vol) were charged into a three-necked round bottom flask equipped with a reflux condenser, overhead stirrer, and thermometer. The reaction mixture was heated to reflux at 118° C. under a nitrogen atmosphere and refluxed overnight. The reaction mixture was allowed to cool to below 55° C. whereupon water (300 mL, 3 volumes) was added to precipitate out the solid. It was isolated by Buchner filtration and the light yellow solid was washed twice with 25% aqueous 2-butanol (100 mL) and then once with 2-butanol (100 mL) and dried to provide olanzapine in 84% yield (98.7 g).

EXAMPLE 3

4-Amino-2-methyl-10H-thieno-[2,3-b][1,5]benzodiazepine (100 g, 0.38 mol), N-methylpiperazine (250 mL, 2.5 vol) and 2-propanol (200 mL, 2 vol) were charged into a three-necked round bottom flask equipped with reflux condenser, overhead stirrer, and thermometer. The reaction mixture was heated to reflux at 102° C. under a nitrogen atmosphere overnight. The reaction mixture was allowed to cool to below 55° C. whereupon water (250 mL, 2.5 volumes) was added to precipitate out the solid. The light yellow solid was isolated by Buchner filtration and twice washed with 25% aqueous 2-propanol (100 mL) and then once with 2-propanol (100 mL). It was dried in vacuo to provide olanzapine in 86.5% yield (101.7 g).

EXAMPLE 4

4-Amino-2-methyl-10H-thieno-[2,3-b][1,5]benzodiazepine (5 g, 0.02 mol), N-methylpiperazine (12.5 mL, 2.5 vol) and 1-propanol (15 mL, 3 vol) were charged into a three-necked round bottom flask equipped with a reflux condenser, overhead stirrer, and thermometer. The reaction mixture was heated slowly to 110° C. under a nitrogen atmosphere and then refluxed overnight. The reaction mixture was cooled to below 50° C. whereupon water (15 mL, 3 volumes) was added to precipitate out the solid, which was isolated by Buchner filtration. The resulting light yellow solid was washed twice with water (5 mL) and dried to afford olanzapine in 89% yield (5.22 g).

EXAMPLE 5

4-Amino-2-methyl-10H-thieno-[2,3-b][1,5]benzodiazepine (5 g, 0.02 mol), N-methylpiperazine (12.5 mL, 2.5 vol) and ethanol (15 mL, 3 vol) were charged into a three-necked round bottom flask equipped with a reflux condenser, overhead stirrer, and thermometer. The reaction mixture was slowly heated to reflux (94° C.) under a nitrogen atmosphere and kept at this temperature overnight. The reaction mixture was cooled to below 50° C. and water (10 mL, 2 vol) was added to precipitate out the solid, which was isolated by filtration. The light yellow solid was washed twice with water (5 mL) and dried to furnish pure olanzapine in 72% yield (4.2 g).

EXAMPLE 6

4-Amino-2-methyl-10H-thieno-[2,3-b][1,5]benzodiazepine (5 g, 0.02 mol), N-methylpiperazine (12.5 mL, 2.5 vol) and methanol (15 mL, 3 vol) were charged into a three-necked round bottom flask equipped with a reflux condenser, overhead stirrer, and thermometer. The reaction mixture was slowly heated under nitrogen to reflux (75° C.) and kept at this temperature overnight. The reaction mixture was allowed to cool to below 50° C. and water (15 mL, 3 vol) was added. The precipitated light yellow solid was isolated by filtration, then was washed twice with water (5 mL) and dried to provide olanzapine in 74% yield (4.35 g).

As many changes can be made to the invention without departing from the scope of the invention, it is intended that all material contained herein be interpreted as illustrative of the invention and not in a limiting sense.

The invention claimed is:

1. A process for the preparation of olanzapine comprising:
   i) reacting 4-amino-2-methyl-10H-thieno-[2,3-b][1,5]benzodiazepine and N-methylpiperazine in a $C_1$ to $C_4$ alcoholic solvent or mixture at suitable reaction temperature and for a suitable reaction time, ii) cooling the reaction mixture, iii) optionally adding water after cooling of said reaction mixture, and iv) isolating the precipitated olanzapine.

2. The process of claim 1 wherein the alcoholic solvent is selected from the group consisting of methanol, ethanol, n-propanol, 2-propanol, 2-butanol and combinations thereof.

3. The process of claim 1 wherein the alcoholic solvent is methanol.

4. The process of claim 1 wherein the alcoholic solvent is ethanol.

5. The process of claim 1 wherein the alcoholic solvent is n-propanol.

6. The process of claim 1 wherein the alcoholic solvent is 2-propanol.

7. The process of claim 2 wherein the alcoholic solvent is 2-butanol.

8. The process of claim 1, 2, 3, 4, 5, 6 or 7 wherein the reaction time is 5 to 30 h.

9. The process of claim 8 wherein the reaction temperature is about 50° C. to about 150° C.

10. The process of claim 8 wherein the reaction temperature is about 80° C. to about 120° C.

* * * * *